US008147861B2

(12) United States Patent
Jones et al.

(10) Patent No.: US 8,147,861 B2
(45) Date of Patent: Apr. 3, 2012

(54) ANTIMICROBIAL IMPLANT

(75) Inventors: Eric Jones, Limerick (IE); Aiguo Wang, Wayne, NJ (US)

(73) Assignee: Howmedica Osteonics Corp., Manwah, NJ (US)

( * ) Notice: Subject to any disclaimer, the term of this patent is extended or adjusted under 35 U.S.C. 154(b) by 1071 days.

(21) Appl. No.: 11/504,307

(22) Filed: Aug. 15, 2006

(65) Prior Publication Data
US 2008/0050412 A1 Feb. 28, 2008

(51) Int. Cl.
*A61L 33/00* (2006.01)
*A61F 2/02* (2006.01)
*A61K 33/38* (2006.01)

(52) U.S. Cl. ........................ 424/423; 424/618; 427/2.24
(58) Field of Classification Search ........................ None
See application file for complete search history.

(56) References Cited

U.S. PATENT DOCUMENTS

| | | | |
|---|---|---|---|
| 3,605,123 A | 9/1971 | Hahn | |
| 3,806,961 A | 4/1974 | Muller | |
| 3,816,855 A | 6/1974 | Saleh | |
| 4,085,466 A | 4/1978 | Goodfellow et al. | |
| 4,164,794 A | 8/1979 | Spector et al. | |
| 4,202,055 A | 5/1980 | Reiner et al. | |
| 4,218,494 A | 8/1980 | Belmondo et al. | |
| 4,305,340 A | 12/1981 | Iwaki et al. | |
| 4,344,193 A | 8/1982 | Kenny | |
| 4,385,404 A | 5/1983 | Sully et al. | |
| 4,502,161 A | 3/1985 | Wall | |
| 4,636,219 A | 1/1987 | Pratt et al. | |
| 4,644,942 A | 2/1987 | Sump | |
| 4,673,408 A | 6/1987 | Grobbelaar et al. | |
| 4,714,473 A | 12/1987 | Bloebaum | |
| 4,714,474 A | 12/1987 | Brooks, Jr. et al. | |
| 4,719,908 A | 1/1988 | Averill et al. | |
| 4,863,538 A | 9/1989 | Deckard | |
| 4,944,817 A | 7/1990 | Bourell et al. | |
| 4,961,154 A | 10/1990 | Pomerantz et al. | |
| 4,969,907 A | 11/1990 | Koch et al. | |
| 4,990,163 A | 2/1991 | Ducheyne et al. | |
| 5,004,476 A | 4/1991 | Cook | |
| 5,017,753 A | 5/1991 | Deckard | |
| 5,024,670 A | 6/1991 | Smith et al. | |
| 5,031,120 A | 7/1991 | Pomerantz et al. | |
| 5,034,186 A | 7/1991 | Shimamune et al. | |
| 5,053,090 A | 10/1991 | Beaman et al. | |
| 5,067,964 A | 11/1991 | Richmond et al. | |
| 5,076,869 A | 12/1991 | Bourell et al. | |
| 5,080,674 A | 1/1992 | Jacobs et al. | |
| 5,108,432 A | 4/1992 | Gustavson | |
| 5,147,402 A | 9/1992 | Bohler et al. | |
| 5,155,324 A | 10/1992 | Deckard et al. | |
| 5,158,574 A | 10/1992 | Stone | |
| 5,171,282 A | 12/1992 | Pequignot | |
| 5,176,710 A | 1/1993 | Hahn et al. | |
| 5,192,328 A | 3/1993 | Winters | |
| 5,219,362 A | 6/1993 | Tuke et al. | |
| 5,282,861 A | 2/1994 | Kaplan | |
| 5,282,870 A | 2/1994 | Moser et al. | |
| 5,287,435 A | 2/1994 | Cohen et al. | |
| 5,314,478 A | 5/1994 | Oka et al. | |
| 5,323,954 A | 6/1994 | Shetty et al. | |
| 5,358,529 A | 10/1994 | Davidson | |
| 5,368,602 A | 11/1994 | de la Torre | |
| 5,386,500 A | 1/1995 | Pomerantz et al. | |
| 5,398,193 A | 3/1995 | deAngelis | |
| 5,443,510 A | 8/1995 | Shetty et al. | |
| 5,443,518 A | 8/1995 | Insall | |
| 5,490,962 A | 2/1996 | Cima et al. | |
| 5,496,372 A | 3/1996 | Hamamoto et al. | |
| 5,504,300 A | 4/1996 | Devanathan et al. | |
| 5,514,183 A | 5/1996 | Epstein et al. | |
| 5,549,700 A | 8/1996 | Graham et al. | |
| 5,571,185 A | 11/1996 | Schug et al. | |
| 5,571,196 A | 11/1996 | Stein | |
| 5,609,646 A | 3/1997 | Field et al. | |
| 5,616,294 A | 4/1997 | Deckard | |
| 5,640,667 A | 6/1997 | Freitag et al. | |
| 5,648,450 A | 7/1997 | Dickens, Jr. et al. | |
| 5,681,354 A | 10/1997 | Eckhoff | |
| 5,702,448 A | 12/1997 | Buechel et al. | |
| 5,728,162 A | 3/1998 | Eckhoff | |
| 5,735,903 A | 4/1998 | Li et al. | |
| 5,773,789 A | 6/1998 | Devanathan et al. | |
| 5,776,201 A | 7/1998 | Colleran et al. | |

(Continued)

FOREIGN PATENT DOCUMENTS

CA 2295896 7/2000

(Continued)

OTHER PUBLICATIONS

The Metals Handbook, Desk Edition, 2nd Edition, ASM International, 1998, p. 29.
"Direct Generation of Metal Parts and Tools by Selective Laser Powder Remelting (SLPR)", W. Meiners, C. Over, K. Wissenbach, R. Poprawe, pp. 655-661.
Patello-femoral Arthroplasty X-ray Results, Stryker Howmedica Osteonics, date not known.
R.H. Morgan, A.J. Papworth, C. Sutcliffe, P. Fox, W. O'Neill, "High density net shape components by direct laser re-melting of single phase powders," Journal of Materials Science, 37, (2002), pp. 3093-3100.
Dr. Kerron Harvey, producer, Research Intelligence, The University of Liverpool, Issue 13, Jun. 2002.
H.J. Niu and I.T.H. Chang, "Selective Laser Sintering of Gas and Water Atomized High Speed Steel Powders," Scripta Materialia vol. 41, No. 1, (1999), pp. 25-30.

(Continued)

*Primary Examiner* — Shanon A Foley
(74) *Attorney, Agent, or Firm* — Lerner, David, Littenberg, Krumholz & Mentlik, LLP

(57) ABSTRACT

A method of building an orthopedic implant including the steps of mixing a powder having antimicrobial properties with a biocompatible powder to form a mixture. Next, the mixture is deposited on top of a substrate. The substrate may be part of the finished product or only a work platform. The mixture layer is then selectively melted.

27 Claims, 13 Drawing Sheets

U.S. PATENT DOCUMENTS

| | | | |
|---|---|---|---|
| 5,782,908 A | 7/1998 | Cahalan et al. |
| 5,795,353 A | 8/1998 | Felt |
| 5,824,098 A | 10/1998 | Stein |
| 5,824,102 A | 10/1998 | Buscayret et al. |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,989,472 A | 11/1999 | Ashby et al. |
| 6,046,426 A | 4/2000 | Jeantette et al. |
| 6,049,054 A | 4/2000 | Panchison et al. |
| 6,087,553 A | 7/2000 | Cohen et al. |
| 6,096,043 A | 8/2000 | Techiera et al. |
| 6,132,468 A | 10/2000 | Mansmann |
| 6,139,585 A | 10/2000 | Li |
| 6,190,407 B1 | 2/2001 | Ogle et al. |
| 6,206,924 B1 | 3/2001 | Timm |
| 6,206,927 B1 | 3/2001 | Fell et al. |
| 6,215,093 B1 | 4/2001 | Meiners et al. |
| 6,248,131 B1 | 6/2001 | Felt et al. |
| 6,251,143 B1 | 6/2001 | Schwartz et al. |
| 6,261,322 B1 | 7/2001 | Despres, III et al. |
| 6,280,478 B1 | 8/2001 | Richter et al. |
| 6,283,997 B1 | 9/2001 | Garg et al. |
| 6,290,726 B1 | 9/2001 | Pope et al. |
| 6,299,645 B1 | 10/2001 | Ogden |
| 6,355,086 B2 | 3/2002 | Brown et al. |
| 6,371,958 B1 | 4/2002 | Overaker |
| 6,395,327 B1 | 5/2002 | Shetty |
| 6,406,497 B2 | 6/2002 | Takei |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 * | 6/2003 | Barry et al. ............... 424/422 |
| 6,599,301 B2 | 7/2003 | Vibe-Hansen et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,682,567 B1 | 1/2004 | Schroeder |
| 6,686,437 B2 | 2/2004 | Buchman et al. |
| 6,699,252 B2 | 3/2004 | Farr, II et al. |
| 6,709,462 B2 | 3/2004 | Hanssen |
| 6,712,822 B2 | 3/2004 | Re et al. |
| 6,712,856 B1 | 3/2004 | Carignan et al. |
| 6,716,957 B2 | 4/2004 | Tunc |
| 6,770,099 B2 | 8/2004 | Andriacchi et al. |
| 6,846,329 B2 | 1/2005 | McMinn et al. |
| 6,850,125 B2 | 2/2005 | Norman et al. |
| 6,855,165 B2 | 2/2005 | Fell et al. |
| 6,866,684 B2 | 3/2005 | Fell et al. |
| 6,893,463 B2 | 5/2005 | Fell et al. |
| 6,911,044 B2 | 6/2005 | Fell et al. |
| 6,916,341 B2 | 7/2005 | Rolston |
| 6,921,264 B2 | 7/2005 | Mayer et al. |
| 6,923,831 B2 | 8/2005 | Fell et al. |
| 6,932,610 B2 | 8/2005 | Ono et al. |
| 7,168,283 B2 | 1/2007 | Van Note et al. |
| 7,494,507 B2 | 2/2009 | Dixon et al. |
| 7,674,517 B2 | 3/2010 | Ramsey et al. |
| 2001/0014403 A1 | 8/2001 | Brown et al. |
| 2002/0010512 A1 | 1/2002 | Takei |
| 2002/0015654 A1 | 2/2002 | Das et al. |
| 2002/0016635 A1 | 2/2002 | Despres et al. |
| 2002/0127328 A1 | 9/2002 | Shetty |
| 2002/0130112 A1 | 9/2002 | Manasas et al. |
| 2002/0151983 A1 | 10/2002 | Shetty |
| 2002/0173855 A1 | 11/2002 | Mansmann |
| 2002/0198528 A1 | 12/2002 | Engh et al. |
| 2003/0033018 A1 | 2/2003 | Merchant |
| 2003/0045941 A1 | 3/2003 | Lewallen |
| 2003/0055500 A1 | 3/2003 | Fell et al. |
| 2003/0055501 A1 | 3/2003 | Fell et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0060888 A1 | 3/2003 | Fell et al. |
| 2003/0069638 A1 | 4/2003 | Barlow et al. |
| 2003/0069718 A1 | 4/2003 | Hollister et al. |
| 2003/0153977 A1 | 8/2003 | Suguro et al. |
| 2003/0153981 A1 | 8/2003 | Wang et al. |
| 2003/0155686 A1 | 8/2003 | Hawkins et al. |
| 2003/0158606 A1 | 8/2003 | Coon et al. |
| 2003/0220696 A1 | 11/2003 | Levine et al. |
| 2004/0006393 A1 | 1/2004 | Burkinshaw |
| 2004/0009228 A1 * | 1/2004 | Tormala et al. ............... 424/486 |
| 2004/0044414 A1 | 3/2004 | Nowakowski |
| 2004/0054416 A1 | 3/2004 | Wyss et al. |
| 2004/0059356 A1 | 3/2004 | Gingras |
| 2004/0098132 A1 | 5/2004 | Andriacchi et al. |
| 2004/0143339 A1 | 7/2004 | Axelson et al. |
| 2004/0153163 A1 | 8/2004 | Posner |
| 2004/0162622 A1 | 8/2004 | Simon et al. |
| 2004/0167633 A1 | 8/2004 | Wen et al. |
| 2004/0191106 A1 | 9/2004 | O'Neill et al. |
| 2004/0199249 A1 | 10/2004 | Fell |
| 2004/0199250 A1 | 10/2004 | Fell |
| 2004/0204766 A1 | 10/2004 | Siebel |
| 2004/0243237 A1 | 12/2004 | Unwin et al. |
| 2004/0267363 A1 | 12/2004 | Fell et al. |
| 2005/0033424 A1 | 2/2005 | Fell |
| 2005/0043816 A1 | 2/2005 | Datta et al. |
| 2005/0079200 A1 * | 4/2005 | Rathenow et al. ............ 424/423 |
| 2005/0085918 A1 | 4/2005 | Soffiati et al. |
| 2005/0100578 A1 | 5/2005 | Schmid et al. |
| 2005/0123672 A1 | 6/2005 | Justin et al. |
| 2005/0154471 A1 | 7/2005 | Aram et al. |
| 2005/0170159 A1 | 8/2005 | Ramsey et al. |
| 2005/0171604 A1 | 8/2005 | Michalow |
| 2005/0177169 A1 | 8/2005 | Fisher et al. |
| 2005/0192672 A1 | 9/2005 | Wyss et al. |
| 2006/0045903 A1 | 3/2006 | Kadiyala et al. |
| 2006/0147332 A1 | 7/2006 | Jones et al. |
| 2007/0142914 A1 | 6/2007 | Jones et al. |
| 2007/0156249 A1 | 7/2007 | Lawrynowicz et al. |
| 2007/0225390 A1 | 9/2007 | Wang et al. |
| 2008/0004709 A1 | 1/2008 | O'Neill et al. |
| 2008/0161927 A1 | 7/2008 | Savage et al. |
| 2009/0068245 A1 | 3/2009 | Noble et al. |
| 2009/0087605 A1 | 4/2009 | Ramsey et al. |

FOREIGN PATENT DOCUMENTS

| | | |
|---|---|---|
| EP | 0 178 650 A2 | 4/1986 |
| EP | 0 528 800 | 3/1993 |
| EP | 0761242 | 3/1997 |
| EP | 1418013 | 5/2004 |
| EP | 1493455 A2 | 1/2005 |
| EP | 1683593 | 7/2006 |
| EP | 1806154 | 7/2007 |
| EP | 1949989 A1 | 7/2008 |
| RU | 2218242 | 12/2003 |
| WO | 9606881 A2 | 3/1996 |
| WO | 2005087982 | 9/2005 |
| WO | 2007058160 A1 | 5/2007 |

OTHER PUBLICATIONS

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.

Structural mechanical and in vitro characterization of individually structured Ti-Al-4V produces by direct layer forming, (2005).

Vureal et al., Plasma-sprayed oxide ceramics on steel substrates, Surface Coatings and Technology, 97 (1997) 347-354.

European Search Report and Written Opinion, EP05028133, dated May 11, 2010.

European Search Report and Written Opinion, EP10162970, dated Jun. 17, 2010.

R. Morgan, C.J. Sutcliffe, W. O'Neill, "Experimental investigation of nanosecond pulsed Nd:YAG laser re-melted pre-placed powder beds," Rapid Prototyping Journal, vol. 7, No. 3, 2001, pp. 159-172.

N. K. Vail, L.D. Swain, W.C. fox, T.B. Aufdlemorte, G. Lee, J.W. Barlow, "Materials for biomedical applications," Materials and Design, 20, 1999, pp. 123-132.

K. Harvey (producer), "Fast masters," Research Intelligence, a publication of the University of Liverpool, Issue 13, Jun. 2002, pp. 1-8.

European Search Report and Written Opinion, EP06127218, dated May 6, 2010.

C.K. Chua et al. Development of a Tissue Engineering Scaffold Structure Library for Rapid Prototyping. Parts 1 and 2, International Journal of Advanced Manufacturing Technology, (2003) vol. 21, pp. 291-312.

Meiners W, Over C, Wissenbach K, Poprawe R., Direct generation of metal parts and tools by selective laser powder remelting (SLPR). Proceedings of SFF, Austin, Texas, Aug. 9-11, 1999.

PCT/US2008/008955 International Preliminary Report on Patentability mailed Feb. 4, 2010.

PCT/US2008/008955 International Search Report and Written Opinion mailed Dec. 2, 2008.

* cited by examiner

Comparison of ODs (600nm) of *Pseudomonas aeruginosa* in contact with Ti SLM coupons at different time periods

ANTIMICROBIAL IMPLANT

BACKGROUND OF THE INVENTION

The present invention is directed to antimicrobial implants and methods of manufacturing the same.

It has become common to treat a variety of medical conditions by introducing an implantable medical device partly or completely into the human body. For example, orthopedic devices are commonly inserted into joints such as the knee, spine, shoulder and the like. Additional orthopedic devices are often implanted adjacent bone such as metal plates during fracture repair and spinal rods for the re-alignment of the spine. Many other implants are used for implantation into the esophagus, trachea, colon, biliary tract, urinary tract, vascular system or other locations within a human or even a veterinarian patient.

One disadvantage associated with implantable medical devices is microbial adhesion. Microbial adhesion occurs when unwanted parasites adhere to the orthopedic implant either during implantation or afterwards.

Microbial adhesion to the surface of an implant device that eventually lead to biomaterials-related infections is a well recognized complication of implant materials and devices. Once adhesion has occurred, proliferation of the microbial agents leads to the development of a biofilm, which is unsusceptible to most therapeutic agents at achievable concentrations. Thus, the course of microbial infection involves three major steps: microbial adhesion; microbial proliferation; and formation of a bacterial bio-film.

Unfortunately, only a few materials, as for instance, gold, silver or copper, show toxicity against microorganisms and biofilm formation. Gold, silver and copper ions are believed to have broad spectrum anti-microbial activity. Of all the metal ions, silver exhibits a high toxicity for microorganisms and is one of the least toxic to animal cells. Still, silver ion concentrations higher than 10 mg/l may be toxic to certain human cells.

It has therefore been known in the art to apply an antimicrobial coating that includes metal ions and specifically silver at low concentrations to combat microbial adhesion.

Still, additional antimicrobial compositions and different ways for incorporating the antimicrobial with orthopedic implants are required.

SUMMARY OF THE INVENTION

The present invention includes a method of building an orthopedic implant including the steps of mixing a powder having antimicrobial properties with a biocompatible powder to form a mixture. Next, the mixture is deposited on top of a substrate. The substrate may be part of the finished product or only a work platform. The mixture layer is then selectively melted.

The method may also include depositing at least one additional layer of mixture and selectively melting the at least one additional layer. The powder is preferably silver in one aspect of the present invention. The silver may be approximately between 0.05% to 9.0% of the mixture. The steps of depositing at least one additional layer of the mixture and selectively melting the at least one additional layer of the mixture and repeating until an orthopedic implant is built.

The method may include depositing at least one layer of biocompatible powder onto either the substrate or a previous layer of the mixture and selectively melting the at least one layer of biocompatible powder. The deposited layers of mixture maybe selectively melted to obtain a component having a predetermined porosity at predetermined locations.

In an alternate embodiment, the method of building an orthopedic implant may include the steps of forming a layer of material that includes a biocompatible powder and an antimicrobial powder; and selectively melting the layer of material at predetermined locations. The steps are preferably repeated at least once. The step of forming the layer of material may include depositing the antimicrobial powder and biocompatible powder simultaneously. The method may further include depositing a layer of biocompatible powder adjacent the layer of material that includes the biocompatible material and antimicrobial powder, and selectively melting the layer of biocompatible powder. The layer of biocompatible material and antimicrobial is deposited onto a portion of an orthopedic implant. The selectively melting of the product may be done by a high energy source such as a laser or e-beam.

In an alternate embodiment, a method of building an orthopedic implant includes the steps of depositing a biocompatible material and selectively melting the biocompatible material and depositing an antimicrobial material and selectively melting the antimicrobial material.

The present invention also includes an orthopedic implant having a biocompatible material fused to an antimicrobial material, wherein the antimicrobial material retains its elemental characteristics. The antimicrobial material may be substantially disposed throughout the orthopedic implant. And may be less than less than 9% of a total composition of the orthopedic implant.

In yet another alternate embodiment, a method of building an orthopedic implant includes the steps of forming a particle mixture containing biocompatible particles and particles having antimicrobial properties; and spraying the particle mixture at a predetermined high velocity toward at least one portion of a surface of a substrate so as to enable a layer of the reactive material to accumulate on the at least one portion of the surface of the substrate.

DETAILED DESCRIPTION

Figure 1:
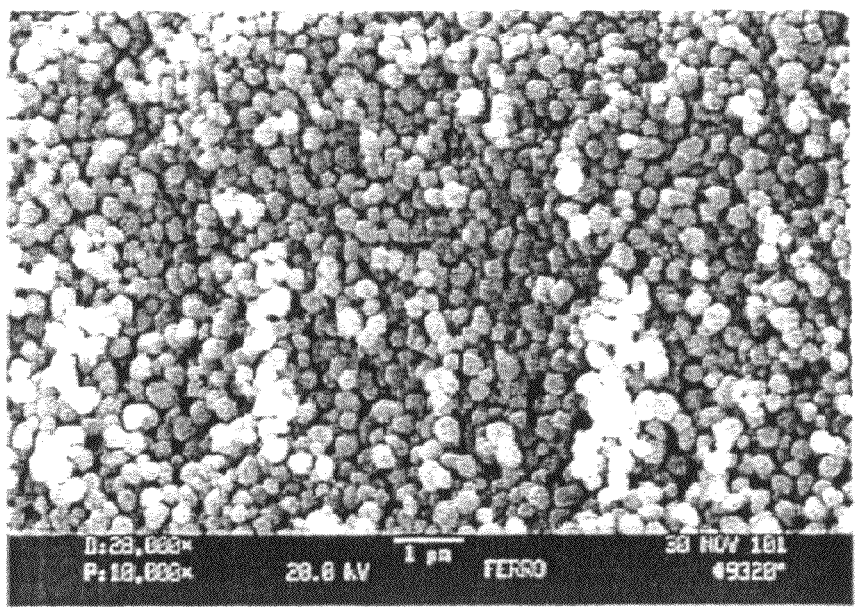
FIG. 1 is an SEM image of an antimicrobial powder used in the present invention.

The present invention combines a rapid manufacturing technique such as "Selective Laser Melting" (S.L.M.) with an antimicrobial material. Selective Laser Melting is often employed to produce devices, which may be implanted within a patient. According to the present invention, the Selective Laser Melting or Sintering Techniques commonly known, are modified so as to incorporate a metal, such as silver, into a build structure of the implantable device. The Selective Laser Melting or Sintering Processes may be similar to U.S. patent application Ser. Nos. 10/704,270 and 11/027,421, the disclosures of which are hereby incorporated by reference herein.

Generally speaking, SLM includes depositing a layer of powder onto a plate or substrate and selectively melting predetermined locations of the layer of powder. A subsequent layer of powder is deposited onto the previous layer of powder and also subjected to selective lasering. This layer-by-layer depositing and selectively lasering technique is repeated until a component part, such as an orthopedic implant, is built. Often, the powder employed is titanium or a similar biocompatible metal.

The component part may have a relatively high density such that only the exterior of the component part is subjected to external forces. However, in certain embodiments the component part may have a porosity and specifically a porosity that promotes bone ingrowth. A porous component part enables a larger surface area of the component part to interact with the outside environment of the component part. For instance if an orthopedic implant built with silver and titanium is completely dense only the silver positioned adjacent the exterior surface of the component part will provide an antimicrobial effect. But if the component part is porous, such as that described in U.S. patent application Ser. Nos. 10/704, 270 and 11/027,421, the silver throughout the component part may aid in providing an antimicrobial treatment.

According to one embodiment of the present invention, a batch of titanium powder was intermixed with a batch of silver powder, such that each layer of the orthopedic implant includes titanium and silver intermixed. Of course, the composition of each layer is dependant on the amount of silver powder and titanium powder mixed as well as whether a complete mixing of the two elements was performed. The characteristics of the titanium powder used for the composition are illustrated in Tables 1, 2 and 3, listed below.

TABLE 1

Composition and Size Distribution of Titanium Powder

| Material description | Specification | Size |
| --- | --- | --- |
| CpTi Grade 2 powder | ASTM B 348/RP 5003 Rev. 1 | −45 microns |

TABLE 2

Chemical Composition of Titanium Powder

| | Element | | | | | | | | | | |
| --- | --- | --- | --- | --- | --- | --- | --- | --- | --- | --- | --- |
| | $N_2$ | C | $H_2$ | Fe | $O_2$ | Al | V | Sn | Mo | Cu | Zr |
| Required, % | <0.03 | <0.1 | <0.015 | <0.3 | <0.25 | ... | ... | ... | ... | ... | ... |
| Results, % | 0.001 | 0.01 | 0.0015 | 0.04 | 0.11 | 0.04 | 0.01 | 0.01 | <0.01 | <0.01 | <0.01 |

| | Element | | | | | | |
| --- | --- | --- | --- | --- | --- | --- | --- |
| | Mn | Ni | Cr | Y | Si | Pd | W | Titanium |
| Required % | ... | ... | ... | ... | ... | ... | ... | Balance |
| Results, % | <0.01 | 0.02 | 0.01 | 0.01 | <0.01 | <0.01 | <0.01 | Balance |

TABLE 3

Size distribution

| Size distribution | Required, % | Results, % |
| --- | --- | --- |
| +45 | Max. 5 | 3.0 |
| −45 | Min. 95 | 97.0 |

As can be ascertained by a review of Table 2, the powder employed includes various other elements such as nitrogen, carbon, helium, and the like, but at relatively low levels. The titanium powder makes up more than 99% of the chemical composition.

In addition, Table 3 illustrates that 97% of the individual "beads" in the titanium powder are less than 45 while only 3% of the batch included microns of titanium beads greater than 45 microns.

The batch of silver powder was then combined with the titanium powder so as to form a mixture. The properties and particle size distribution of the silver powder is shown in Table 4.

TABLE 4

Properties of Silver Powder

Physical data:

Tap Density - standard test:- 3.4 grams/cc
Surface Area: 2.71 $m^2$/gm
Losses: As you heat it up lose $H_2O$ 110° C. loss - 1 hour in air: 0.13
538° C. loss - ½ hour in air: 0.43%%
Particle size distribution:

95%: 0.55 μm
90%: 0.45 μm
50%: 0.30 μm
10%: 0.21 μm

As illustrated in Table 4, a certain percentage of the silver by weight is lost as the silver is heated. This is a result of water loss during a heating process. The particle size distribution is interpreted in that 95% of the silver particles are less than 55 Microns, 90% are less than 46 Microns, and so forth.

FIG. 1 illustrates an SEM image of the silver powder mixture used in the process. The preparation of the titanium-silver mixture was conducted in a ball mill. First, the batches of titanium and silver powder were mixed in a cylinder of the ball mill. The cylinder was then sealed with black tape so that the powder was prevented from escaping. Once the cylinder was properly placed, the ball mill machine was switched on, and allowed to run for numerous hours. The extended length of the ball milling process was preferred in order to make sure a complete homogenous mixture of the titanium and silver powder was reached. The specifications of the milling process are listed below in Table 5.

TABLE 5

Powder Mixing Parameters

| | |
|---|---|
| Type of the ball mill | Planetary |
| Cylinder height | 230 mm |
| Cylinder diameter | 75 mm |
| Rotational speed | 60 rpm |
| Milling time | ~17 hours |
| Size of balls in ball mill | 10-20 mm diameter |
| No. of balls used | 18 |

Once the titanium-silver powder was prepared, various parts such as coupons were manufactured using the mixed powder in the SLM process. The coupons have rectangular shapes with a height of 9 mm, a width of 9.5 mm and a thickness of 3 mm. The manufacturing of the coupons was conducted using an SLM machine and MCP Realizer, which is a product of Mining and Chemical Products, Ltd.

Figure 2:
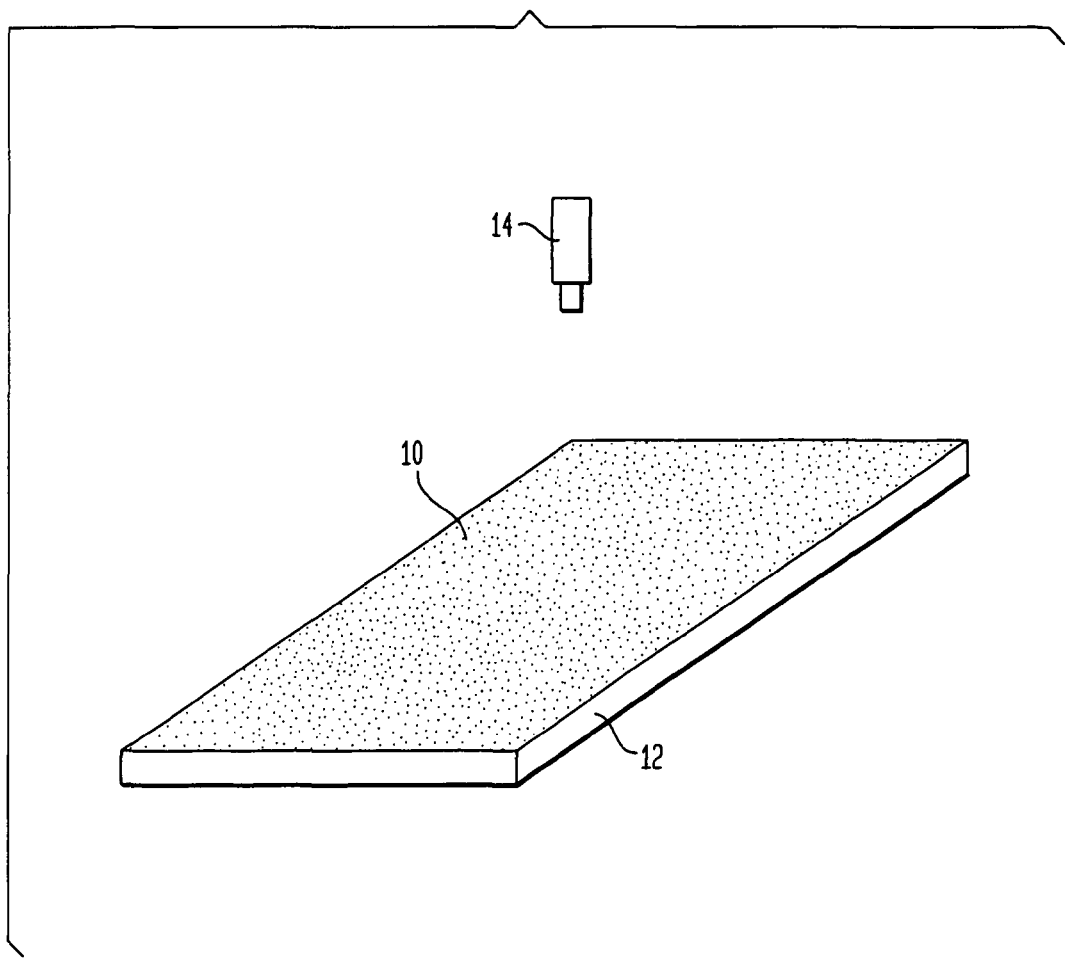
FIG. 2 is a perspective view of an apparatus used in connection with the present invention.
Figure 3A:
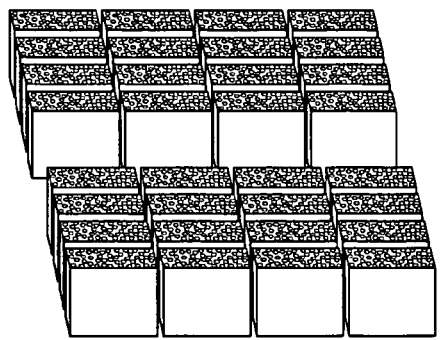
FIGS. 3A-4C are various views of coupons built using one embodiment of the present invention.
Figure 3B:
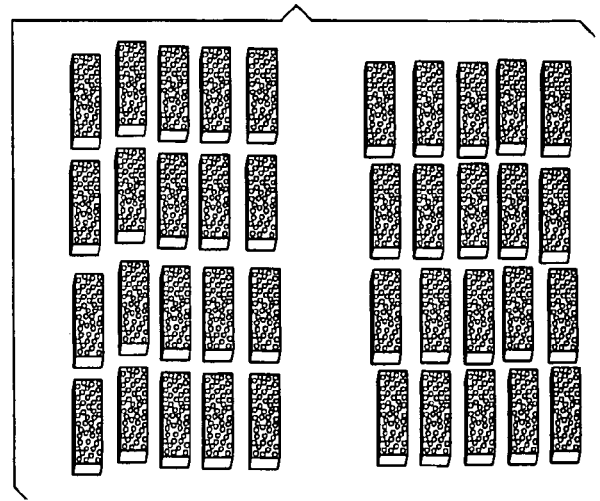
Figure 3C:
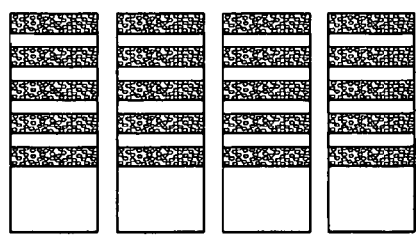
Figure 3D:
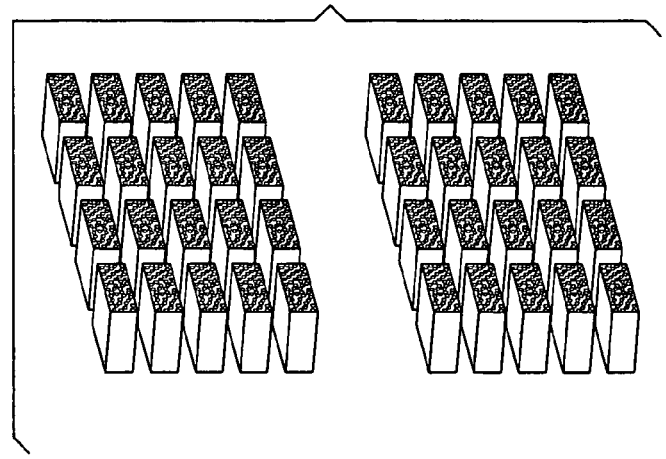
Figure 4A:
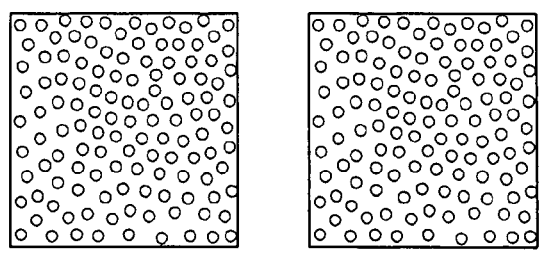
Figure 4B:
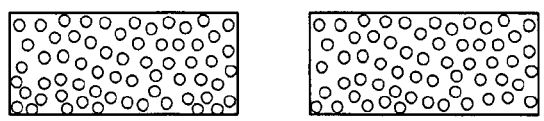
Figure 4C:
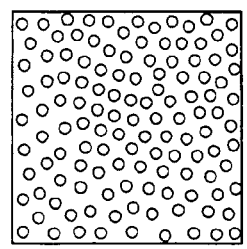
Figure 4C:
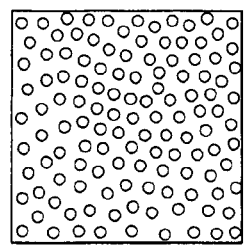

The principal operation of the machine is illustrated in FIG. 2. During the manufacturing process, a layer of the mixed powder 10 is placed on a substrate or plate 12. The substrate or plate 12 may be part of the finished product or only a preparation platform for the finished product. Once a layer of powder 10 has been deployed, a laser 14 scans the powder at pre-determined locations. Various computer programs and the like may be utilized during this process to control and direct the laser. This process used for manufacturing the coupons was conducted in a chamber that was sealed from the outside environment and made inert by argon gas. The gas pressure of the chamber was reduced to approximately 30 mbar. The manufacturing parameters were controlled by the software FUSCO, a machine operating system, which is incorporated into the SLM machine. The process parameters employed for making the various coupons are shown in Table 6. For example, 6 groups of coupons were constructed. Approximately 40 coupons were built, each containing different percentages of silver mixed in with the titanium powder.

Group I—Titanium parts with no Ag
Group II—Titanium parts with 0.05% Ag
Group II—Titanium parts with 0.1% Ag
Group IV—Titanium parts with 0.25% Ag
Group V—Titanium parts with 1% Ag.
Group VI—Titanium parts with one surface being covered with 0.25% Ag plus titanium Groups I-V represent different levels of silver in the compound and where processed using the SLM technique. Group VI was also processed by the SLM process but received a coating of the silver-titanium using a cold spray process. In the cold spray process employed the coupon was produced using the SLM procedure but with pure titanium. Next, powder containing both silver particles and titanium particles was disposed on the surface of the coupons using a cold spray process as discussed in U.S. patent application Ser. No. 11/325,790 the disclosure of which is incorporated by reference herein.

In alternate embodiment, the total construct of the coupons could have been produced using the cold spray process. Of course different portions of the total construct could be produced with different types of powder to give the construct an uneven blend of titanium and silver powder.

In both the cold spray process and the selective laser melting or sintering process the silver maintains its elemental characteristics. And as such does not form an alloy with the titanium or any other metal that may be used. If an alloy was formed, the effectiveness of the silver to act as an antimicrobial agent will be reduced.

TABLE 6

| | |
|---|---|
| Laser | Yttrium doped fiber laser (wavelength: 1.06 μm) |
| Power | 30 W |
| Dwell time | 5500 μs |
| Spot size | 30 μm |
| Thickness of one layer | 75 μm |
| No. of layers | 128 |
| Gas pressure | $O_2$ - 0.2%; Pressure - 27 mbar |
| Process duration | ~3.5 hrs |

Once completed, the collected coupons were then cleaned by an ultrasonic bath cleaning using a detergent. The cleaning process was carried out for approximately 30 minutes. The cleaned coupons were then washed with acetone and dried. As shown in FIGS. 3A-D and FIGS. 4A-C, the various coupons have a lattice-like structure with a pre-determined porosity.

Figure 5:
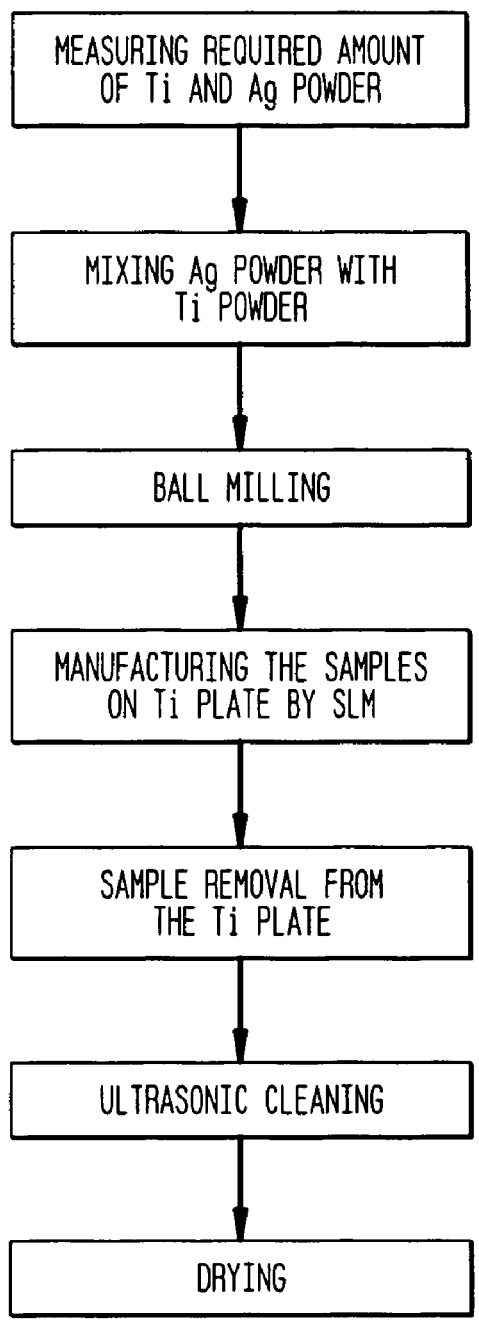
FIG. 5 is a graph illustrating the steps of an embodiment of the present invention.

With reference to FIG. 5, a flow-chart is used to illustrate the various steps for preparing the coupons.

Once the coupons were constructed, as well as during construction, four different types of tests were performed: elemental analysis; cytotoxicity; dissolution rate test; and biofilm assay.

First, the elemental analysis was conducted for the various materials and parts. The analysis was carried out by Inductivity Coupled Plasma-Mass Spectrometry "ICPMS" to determine: the composition of the blended powder; the composition of the processed parts; and the concentration of ions in the physiological solutions at various time intervals to determine the rate of silver ion leaching.

Figure 6:
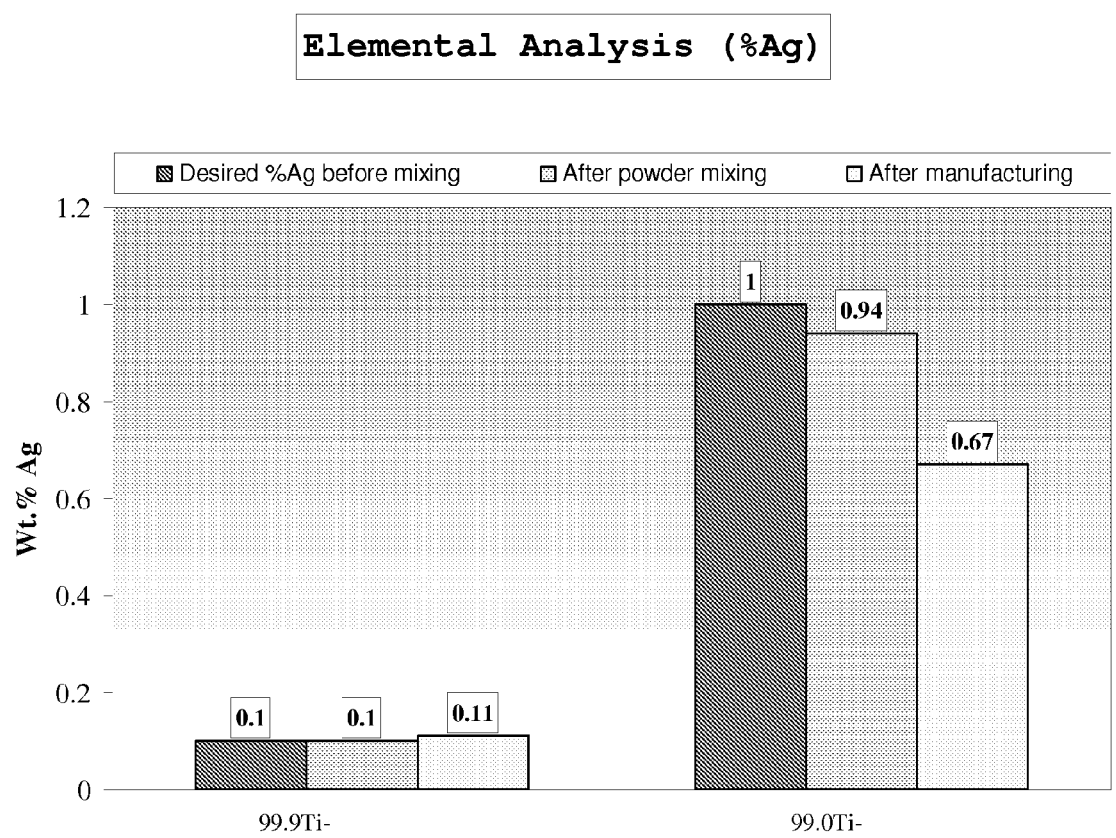
FIG. 6 is a bar graph presenting results of an elemental analysis experiment.
Figure 7:
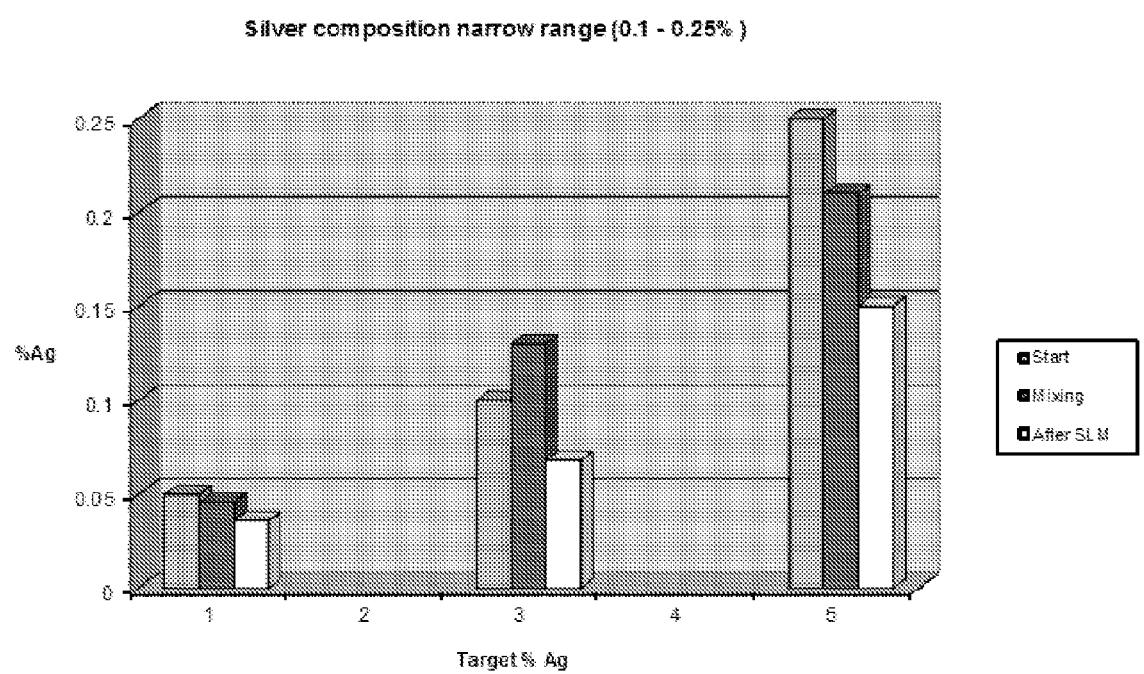
FIG. 7 is a bar graph presenting results of another elemental analysis experiment.

Two sets of data are presented, each representing two different elemental analysis experiments. For example, FIG. 6 includes coupons that were constructed using a mixed Ti/Ag powder where the powder ratio includes silver powder in the range of 0.1-1.0%. FIG. 7 includes data regarding coupons that were constructed with a powder that contained 0 to 0.25% of silver.

The data shows that within each of the groups the amount of silver is reduced during the process from the initial amount of silver powder contained within the intermixed powder to the final percentage of silver in a built part. When considering the final formulation therefore, these expected losses together with other expected losses through post-treatment operations must be taken into consideration in order to attain the desired silver contained in the finished product.

Next, a cytotoxicity test was used to determine the compatibility of the titanium-silver processed coupons with L929 fibroblast; and secondly to distinguish the effect of different percentages of silver within the blended powder on the behavior of the cells. Extracts of the various coupons containing different percentages of silver were added to the fibroblast cells. MTT assay, which measures cell proliferation, was used in this study. Once the MTT is added to the cell culture, it is modified into a dye by enzymes associated with the metabolic activity of the live cells, and the density of this dye is monitored using a spectrometer at a specified wavelength. A ratio of 0.1 g/ml was used for preparing the extract solutions with water being added to 0.1 g of each extract to achieve 1 ml solutions. This ratio was taken from the standard ISO 10993-12:20004-biological evaluation of medical devices: part 12: sample preparation and reference materials. The resultant solutions were then put into individual wells on a plate.

Figure 8:
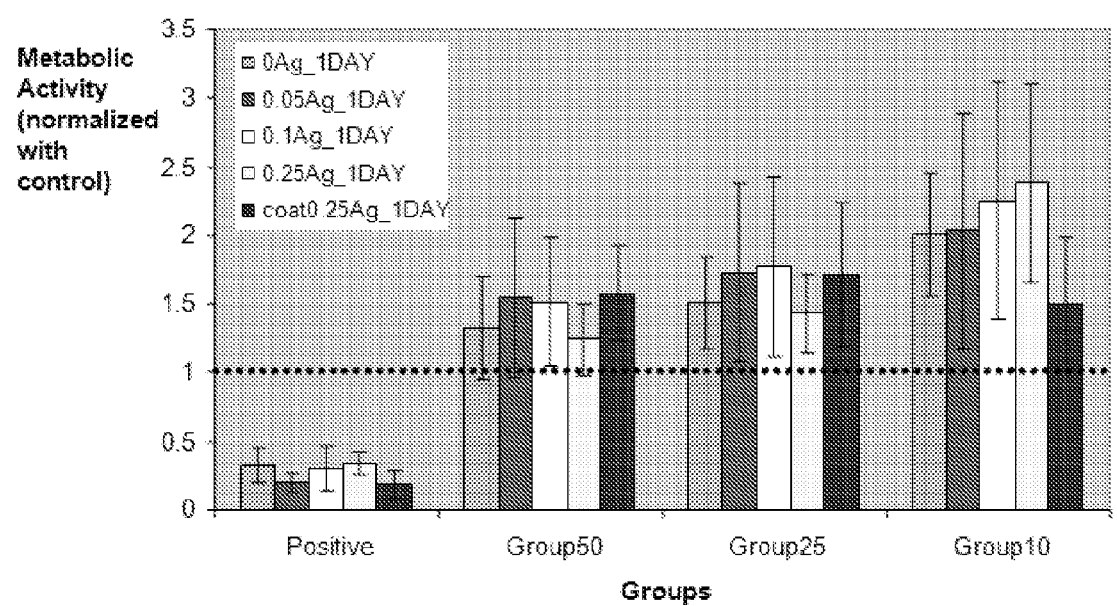
FIG. 8 is bar graph presenting results of a cytotoxicity test after a first time interval.
Figure 9:
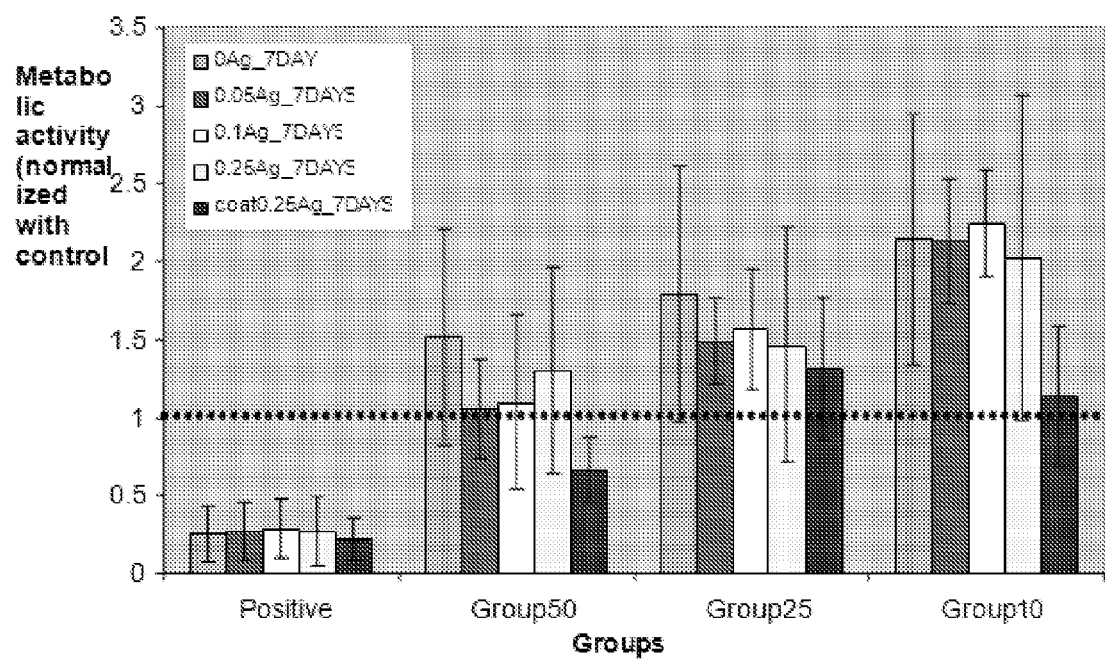
FIG. 9 is a bar graph presenting results of the cytotoxicity test for which the results were presented in FIG. 8 after a second time interval.

FIGS. 8 and 9 represent the data produced by the MTT assays on L929 fibroblasts with the extracts of the different groups of titanium-silver SLM samples. The two figures represent the normalized data for the different time conditions and different groups. The X-axis of each figure corresponds to the different extracted groups per plate. The dotted lines in each figure give an indication of cell proliferation. Anything below the lines indicates that cells are not proliferating.

FIG. 8 illustrates the metabolic activity of L929 fibroblasts after 1 day while FIG. 9 represents the same experiment after days.

FIG. 8 illustrates that the 1 day extracts of SLM samples with silver did not induce any cytotoxic effect. It was observed that there was an increase on the metabolic activity of the L929 fibroblasts, which is closely related to the number of live cells per well.

Similarly, FIG. 9 illustrates that the samples did not induce any cytotoxic effect after days. And it was observed that there was an increase on the metabolic activity of the L929 fibroblasts. Coupons with 0% Ag and 0.25% Ag had similar effects on the metabolic activity of the fibroblasts. Coupons with 0.05% Ag and 0.1% Ag groups demonstrated a similar pattern in relation to the metabolic activity of the L929 fibroblasts as shown from Group 50 (50% Dilution) in FIG. 9. The coupons with 0.25% Ag coated Ti SLM samples had a similar metabolic effect to the controls (dotted line) at its lower dilutions. At its 50% dilution (highest concentrated extract) the group of coated samples induced a cytotoxic effect to the fibroblasts.

A comparison between the 1 and 7 days extracts showed a similar pattern, with all the groups being compatible with the L929 fibroblasts at both time periods. On a more detailed approach it was observed that the coupons with 0% Ag and 0.25% Ag stimulated a similar effect to the metabolic activity of the fibroblasts. These groups showed a higher cytocompatible effect with the 7-days extracts than with the 1-day extracts. Thus, the extraction time for these groups is an important factor for their cytocompatibility properties. However, the coupons containing the 0.05% Ag, 0.1% Ag and the 0.25% Ag coating groups caused different effects on the metabolic activity of the cells at the two time periods. The metabolic activity of the fibroblasts in contact with the 7-days extracts of the above groups was decreased in comparison with the 1 day extracts of the same groups.

Other research groups similarly support findings of this study such that not only are the coupons not cytotoxic but they are in favor of increasing the cell behavior comparison with their control group.

Figure 10:
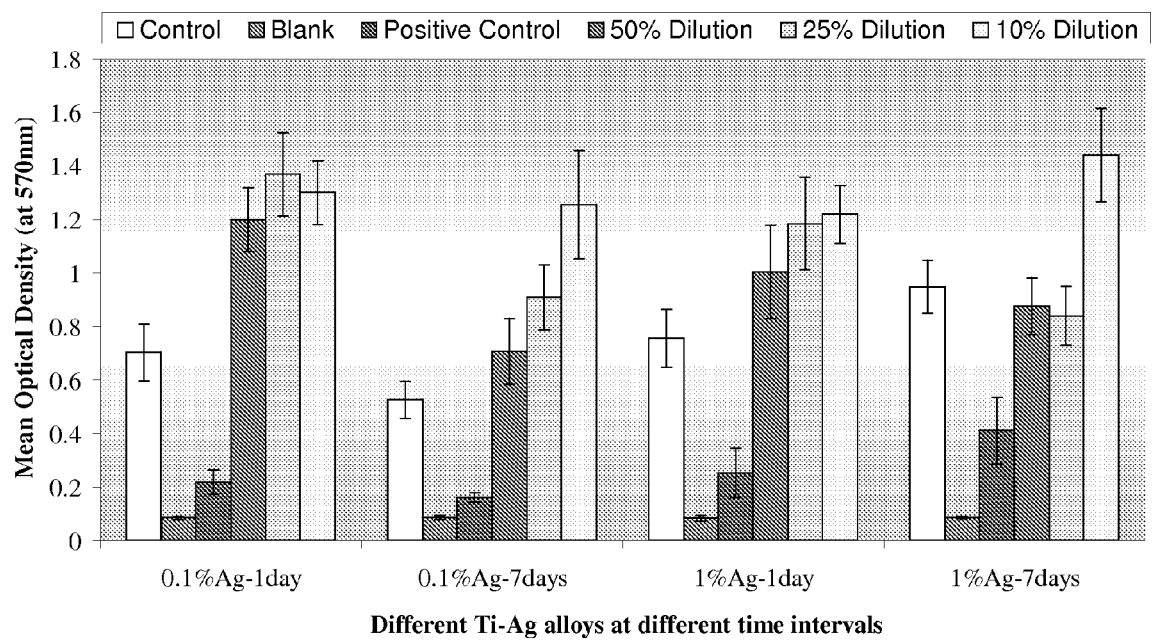
FIG. 10 is a bar graph presenting results of another cytotoxicity test.

Cytotoxicity tests were also carried on the range of coupons that included silver compositions extending from 0.1 to 1.0%. This data for 1 and days contact with fibroblasts is illustrated in FIG. 10.

The control group (L929 fibroblasts in medium) was the ideal environment for the cells. The cells were growing and proliferating on the surface of the wells. Conversely, latex the positive control, provided hostile environment for cell proliferation. The columns in FIG. 10 that extend above that of the control columns indicate that that there was an increase in the number of cells i.e. the cells were proliferating. The environment was favorable to cell growth and the cells were compatible with the environment of the extract group. The columns that are below the control columns in FIG. 10 indicate that there was an inhibitory effect on the behavior of the cells. The environment was aggressive for cell growth. Cells did not proliferate as the cells were not compatible with the environment.

One day and seven days extracts containing 0.1% Ag did not show any cytotoxicity. And one day extracts containing 1.0% Ag also did not show any cytotoxicity.

When the test was conducted for 7 days on the same extracts, there was mild cytotoxicity observed in the case of 25% and 50% dilutions. It may be concluded that with higher amounts of silver, cytotoxicity is more susceptible with the course of time. But it must be kept in mind that these cells have not been subjected to nutrition, and therefore cell death will occur in any event. Other research groups have found that no cytotoxicity occurred when Ti alloy with 1.0% Ag, was evaluated by Agar Overlay Test. However, they observed mild cytotoxicity with increasing the amount of silver, from 2.0% upwards.

Next, a dissolution rate test was conducted on the 6 different groups of coupons. The dissolution rate test was carried out to measure the amount of silver and titanium released from the coupons.

Ion release from the titanium plus silver parts in Phosphate Buffered Saline (PBS) solution was performed for short-term tests of up to two weeks. The parts were immersed in polypropylene universals (extraction vehicles). A ratio of 0.1 g/ml was used for preparing the extraction solutions.

The Phosphate Buffer Solution was the chosen immersion medium as suggested from the standard I.S.O. 10993-12: 2004. The study was performed at 37° C. Once all the media were collected, they were taken to the elemental analysis room where ICPMS analysis was performed.

Figure 11:
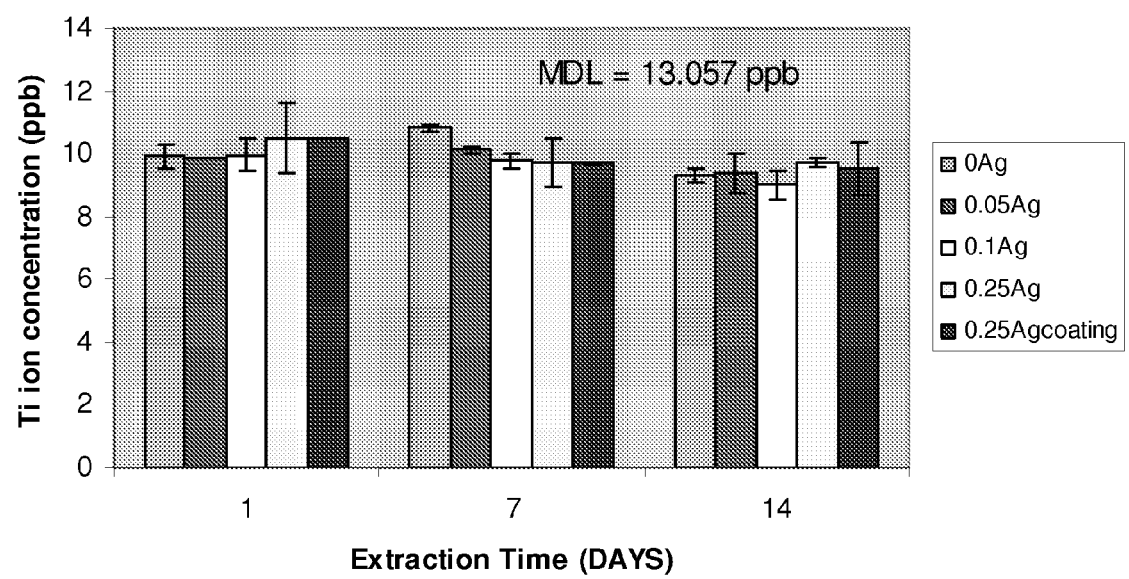
FIG. 11 is a bar graph presenting the number of titanium ions released during cytotoxicity tests as determined by a dissolution rate test.
Figure 12:
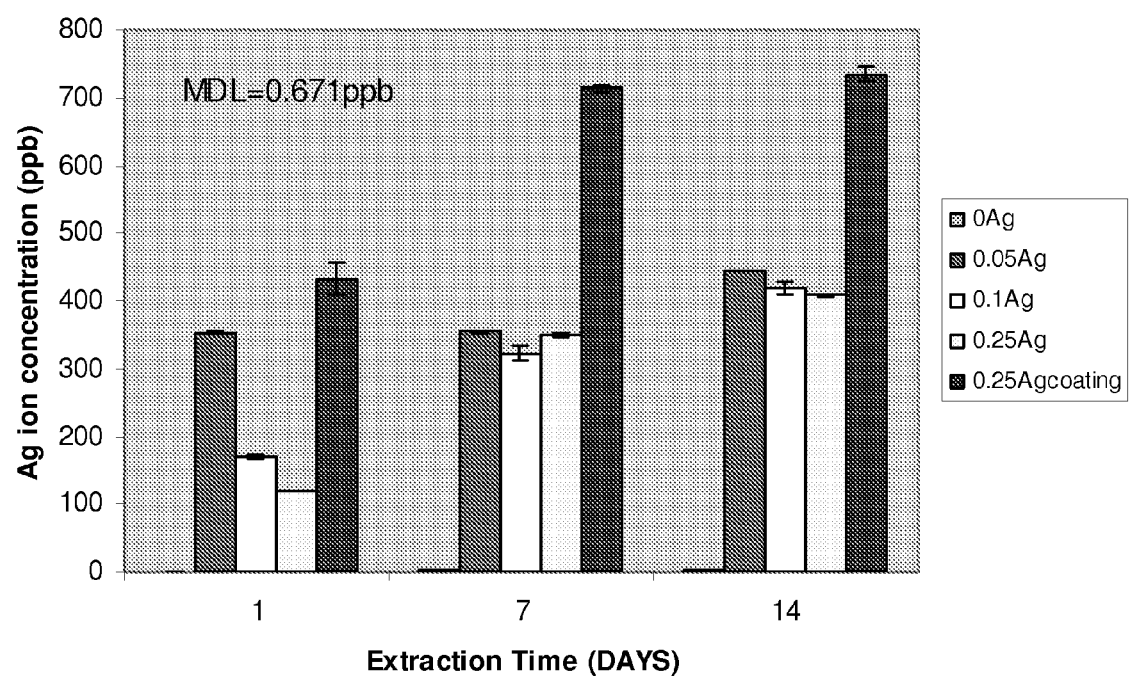
FIG. 12 is a bar graph presenting the number of silver ions released during cytotoxicity tests as determined by a dissolution rate test.

The main findings of ICP-MS on titanium and silver ions released from the processed SLM parts are presented in FIGS. 11 and 12. FIG. 11 illustrates the release of titanium ions from the processed SLM parts by ICP-MS at different time periods. The Method Detection Limit (MDL) for titanium is about 13 ppb. Method Detection Limit (MDL) is based on the mean+ 3.14× the standard deviation of seven controls, which in this case is PBS. FIG. 12 illustrates the release of silver ions from the processed SLM parts by ICP-MS at different time periods. For silver, the detection limit (MDL) is 0.5 ppb. FIG. 11 also shows that the amount of titanium ions released into the medium is lower that the detection limit (MDL) for the titanium isotope. There was a similar amount of titanium ion release for all of the extraction time periods.

The release of silver ions from the different groups was significantly higher than the detection limit as shown in FIG. 12. The coupons constructed without any silver (0% Ag) and only titanium had a negligible amount of silver ions released (and similar to MDL) indicating that no silver ions were released from the coupons. The coupons having 0.05% of silver leached the same concentration of silver ions at one and seven days. The leached amount of silver ions did increase when the immersion time was increased to 14 days. The coupons having 0.1% and 0.25% of silver showed a similar trend on the leaching of silver ions by increasing the immersion time. These two groups released the same ion concentration as coupons having 0.05% of silver at seven days. The coupons having 0.25% silver, which were subjected to a cold spray released the highest concentrations of silver ions. By increasing the immersion time the concentration of released ions was increased.

Generally there was a rapid increase of the release rate of silver ions at seven days compared with the results from day one for all the groups, except for the group with 0.05% silver. The rapid release rate of silver ions could be attributed to the direct contact of the medium with the surface and inner parts of the coupons due to the porosity of the coupons. At fourteen days there was a small increase in the release rate of silver for all of the groups. From FIG. 12 it could be observed that the silver ions release slowed down at fourteen days.

The above findings could be compared with findings from other research groups. Additional studies observed an increased silver ion release and then a marginal increase between 4 to 6 days. It must also be remembered that the silver concentrations represented by the respective figures are not absolute as silver was lost during the processing. It is therefore not surprising that in the short term, the coupons with 0.25% of silver and which were coated gave the highest release of silver, as this was an accurate representation of the silver content, and all of the silver was present on the surface of the coupon.

Antimicrobial properties of silver release were accessed by monitoring biofilm formation resulting from pathogen presents. Biofilm experiments were only carried out on the narrow range of silver addition, specifically coupons that included silver in between the range of 0.05 to 0.25%.

The organism used for this study was *Pseudomonas aeruginosa*. *Pseudomonas aeruginosa* is an opportunistic pathogen, which takes advantage of any break in a host's defenses to initiate an infection. The main causes of this organism are urinary tract infections, respiratory system infections, soft tissues infections, bone and joint infections and gastrointestinal infections. *Pseudomonas aeroginosa* is primarily a nosocomial pathogen. This bacterium is the fourth most commonly isolated nosocomial pathogen accounting for 10.1% of all hospital acquired infections. The bacteriostatic effect of the Ti—Ag coupons was evaluated by determining indirectly the number of bacterial cells in a bacteria culture after selected time periods, the time periods being 0 hours, 6 hours and 24 hours. The indirect determination utilized an optical density measurement. However, a scanning Electron Microscopy (SEM) was used at the end of the experiment to take images of any biofilm formation on the different groups of constructs.

The *Pseudomonas aeruginosa* was cultured in an L-broth for 18 hours before introduction into the test environment. After 18 hours of exposure to the broth, the cell density of the *Pseudomonas aeruginosa* was read at a wavelength of 600 nm (OD600) using a spectrophotometer. Two different dilutions (1/5 and 1/10) were performed in order to obtain an initial OD of 0.1-0.3 according to the standard E2149-01. In order to test direct contact of the bacteria with the coupons, the *Pseudomonas aeruginosa* inoculum was placed in culture flasks together with enough culture medium to cover the individually constructed coupons. All the flasks were incubated at 37° C. with agitation.

After 0 hours an aliquot of media from each flask was recovered and placed in a cuvette (clear plastic containers for the spectrophotometer). A cuvette containing a blank of LB medium was placed in the reader of the spectrophotometer to adjust the reading to zero. Then the cuvette containing an aliquot (1000 μl) of each flask was read. The main reason for this set of readings was to insure that a similar number of bacteria were in each flask. After 6 hours and 24 hours, the same process was repeated. After 6 hours and 24 hours all of the coupons were recovered and prepared for SEM analysis by a standard fixation procedure. All the samples, i.e., coupons were first washed in PBS, and then the coupons were fixed in 2.5% gluteraldehyde solution for 15 minutes. The samples were then dehydrated for 30 minutes each in an ethanol bath at 70%, 90% and 100%, sequentially. All the coupons where then stored in a desiccator. A carbon coater was then used to coat all the samples for SEM analysis.

Figure 13:
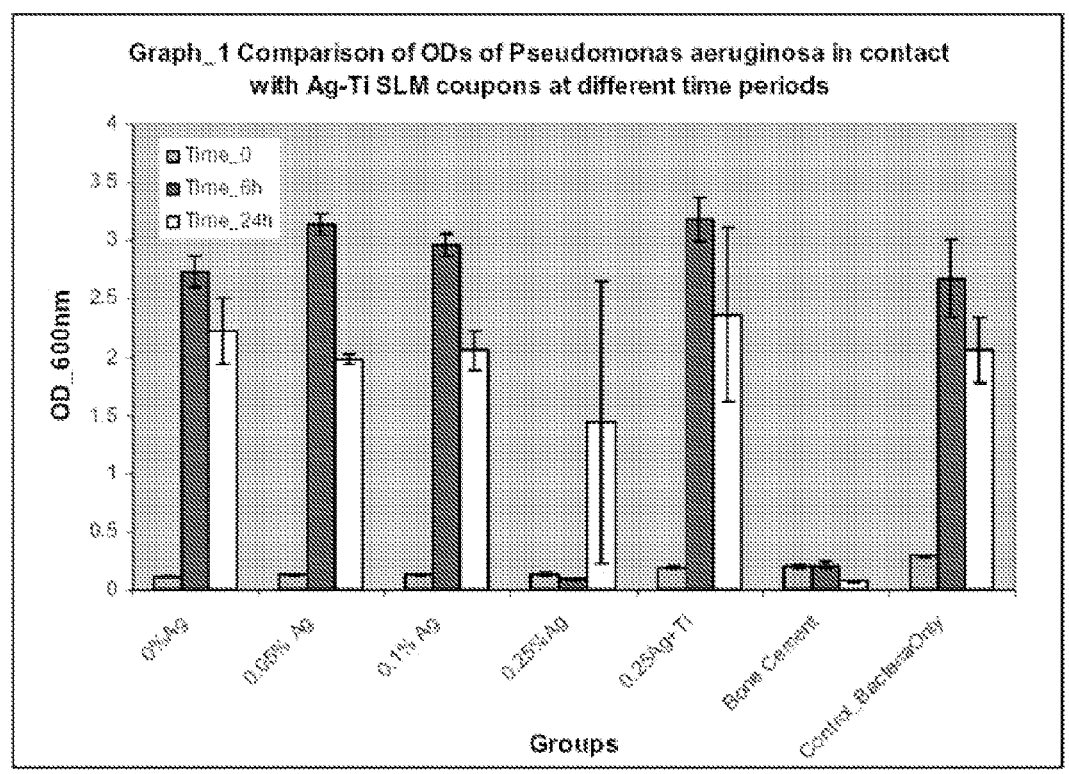
FIG. 13 is a bar graph presenting the results of an optical density test.

An Optical Density (OD) test was performed to determine the cell number of a suspension of cells. Table and FIG. 13 illustrate the effect that the different coupons having a different percentage of silver disposed therein had on the bacteria suspension. The percentage of silver within each coupon is a measurement of the amount of silver in the original mixture prior to any processing. It does not take into account losses of silver during formation of the samples.

TABLE 7

OD (600 nm) of *Pseudomonas aeruginosa* in contact with Ag-Ti SLM coupons at different time periods. The initial OD was 0.106

| Sample_Groups | | 0h 6h_flasks-24h_flasks | | 6 hours | 24 hours |
|---|---|---|---|---|---|
| 0%Ag | A | 0.109 | 0.117 | 2.72 | 2.31 |
| | B | 0.107 | 0.116 | 2.6 | 1.90 |
| | C | 0.121 | 0.115 | 2.875 | 2.45 |
| 0.05%Ag | A | 0.129 | 0.129 | 3.095 | 1.94 |
| | B | 0.132 | 0.123 | 3.24 | 2.02 |
| | C | 0.131 | 0.134 | 3.07 | 1.98 |
| 0.1%Ag | A | 0.128 | 0.130 | 2.97 | 2.25 |
| | B | 0.132 | 0.125 | 2.865 | 1.98 |
| | C | 0.133 | 0.127 | 3.05 | 1.94 |
| 0.25%Ag | A | 0.129 | 0.141 | 0.092 | 2.43 |
| | B | 0.123 | 0.126 | 0.091 | 0.095 |
| | C | 0.121 | 0.148 | 0.086 | 1.80 |
| Coat0.25%Ag | A | 0.170 | 0.191 | 3.16 | 2.22 |
| | B | 0.189 | 0.191 | 3.38 | 3.17 |
| | C | 0.161 | 0.201 | 3.00 | 1.70 |
| Bone Control | A | 0.213 | 0.212 | 0.239 | 0.080 |
| | B | 0.200 | 0.201 | 0.211 | 0.080 |
| | C | 0.174 | 0.181 | 0.172 | 0.071 |
| Control | A (0%) | 0.283 | 0.289 | 2.22 | 1.99 |
| | B (0.05%) | 0.291 | 0.295 | 3.165 | 2.11 |
| | C (0.1%) | 0.281 | 0.287 | 2.805 | 2.37 |
| | D (0.25%) | 0.294 | 0.293 | 2.745 | 2.40 |
| | B (coat0.05%) | 0.288 | 0.294 | 2.395 | 1.70 |
| | C (BoneCement) | 0.292 | 0.296 | 2.69 | 1.82 |

Initially, the OD was obtained from neat solutions (bacteria+broth). At 6 hours time the OD was obtained from 1/5 dilutions (bacteria+broth). And at the twenty four hour mark the OD was obtained from 1/10 dilutions (bacteria+broth). The grey shading in some of the boxes indicates neat solutions.

According to Table 15, at the sixth hour the coupons that showed an effect similar to the control group were the coupons with 0% Ag, 0.05% Ag, 0.1% Ag and 0.25% Ag with a cold spray coating. The bacteria in contact with these coupons proliferated at the same manner as the control groups. There is no statistical difference between the ODs of these groups. However, the 0.25% Ag coupons stopped the bacteria growth. Further, there was no statistical difference between the ODs of this group at the start (0 hour) or at the six hour mark. Therefore the silver released from the 0.25% Ag coupons had an effect on bacteria at 6 hours.

At the twenty-four hour mark coupons with 0% Ag, 0.05% Ag, 0.1% Ag and 0.25% Ag coating all had a bacteria proliferation similar to that of control flasks. The coupons with 0.25% Ag produced different results. One of the three samples prevented the proliferation of bacteria while the other two samples allowed the bacteria to proliferate in a similar manner to the twenty-four hour controls. Thus, the coupons originally created with 0.25% silver but actually with only 0.15% silver due to losses at various stages is an approximation of the lower levels of silver required to effectively prevent bacteria proliferation for the sample geometry. The antibiotic bone cement was used as a control to confirm that bacteria could be killed to prevent formation of the biofilm. A sample of antibiotic bone cement was added into certain wells to obtain this control number.

The absorbencies of the groups at the 6 hour mark were greater than the absorbencies of the groups at twenty four hours. This could be attributed to the fact that these incubation times belong to different stages of the bacteria growth cycle. The initial incubation time belongs to the lag phase of the growth cycle. In this phase there is no apparent cell division occurring, but the cells increase in metabolic activity. The 6 hour incubation time belongs to the exponential (log) phase of the bacteria growth cycle where all the cells divide at a constant rate depending upon the composition of the growth medium and the conditions of incubation. Finally, the twenty-four hour incubation time belongs to the stationary phase of the bacteria growth cycle, which is the stage after the exponential (log) growth phase. During this phase population growth is limited by one of three factors: exhaustion of available nutrients; accumulation of inhibitory metabolites end-products; and/or exhaustion of space. The main finding of the SEM analysis is the formation of biofilm at the periphery of the samples. There is no biofilm formation observed but there are bacteria attached on surface of the samples in all of the groups except the 0.25% Ag group and the Bone Cement group. However, biofilm formation was observed on the samples of the different groups of percentage of Ag—Ti (coupons) samples at the twenty-four hour mark.

These results are indicative that this method has the ability to inhibit/prevent the growth of bacteria, notwithstanding that it is silver concentration and ion release dependent.

Although the present invention has been described using a homogeneous mixture of silver powder and titanium powder—subject to the restrictions of thoroughly mixing the two—in alternate embodiments the composition of the powder may change from layer to layer. For instance, with the SLM process a first number of layers of a component may be built entirely with titanium powder. Then the next layers of the component may be built using a mixture of silver and titanium powder. This process may be alternated until the component part is complete. The percentage of silver within the various layers may also be changed such that some layers have for instance 0.1% silver and others have 0.25% silver. This process may also be incorporated into the cold spray process.

In another aspect of the present invention at least one layer of material used to construct the orthopedic implant includes only silver powder. For example, the orthopedic implant may be built having a layer of silver adjacent layers of titanium. Of course various layers of silver may be positioned together while these layers are positioned adjacent to titanium layers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of building an orthopedic implant comprising the steps of:
    mixing a first powder having antimicrobial properties with a biocompatible second powder to form a mixture;
    depositing a layer of the mixture on top of a substrate; and
    selectively melting the mixture layer,
    wherein at least the second powder is metallic.

2. The method of claim 1,
    further comprising depositing at least one additional layer of mixture and selectively melting the at least one additional layer.

3. The method of claim 1, wherein the first powder includes silver.

4. The method of claim 3, wherein the silver comprises approximately between 0.05% to 9.0% of the mixture.

5. The method of claim 2, wherein the steps of depositing at least one additional layer of the mixture and selectively melting the at least one additional layer of the mixture are repeated until an orthopedic implant is built.

6. The method of claim 2, further comprising depositing at least one layer of biocompatible powder onto either the substrate or a previous layer of the mixture and selectively melting the at least one layer of biocompatible powder.

7. The method of claim 1, wherein the substrate is part of a finished product.

8. The method of claim 2, wherein the deposited layers of mixture are selectively melted to obtain a component having a predetermined porosity at predetermined locations.

9. The method of claim 1, wherein the first powder is metallic.

10. A method of building an orthopedic implant comprising the steps of:
    mixing a first powder having antimicrobial properties with a biocompatible second powder to form a mixture, the first and second powders being metallic;
    depositing a layer of the mixture on top of a substrate; and
    selectively melting the mixture layer through the use of a laser.

11. The method of claim 10, further comprising depositing at least one additional layer of mixture and selectively melting the at least one additional layer.

12. The method of claim 10, wherein the first powder includes silver.

13. The method of claim 12, wherein the silver comprises approximately between 0.05% to 9.0% of the mixture.

14. The method of claim 11, wherein the steps of depositing at least one additional layer of the mixture and selectively melting the at least one additional layer of the mixture repeated until an orthopedic implant is built.

15. The method of claim 11, further comprising depositing at least one layer of biocompatible powder onto either the substrate or a previous layer of the mixture and selectively melting the at least one layer of biocompatible powder.

16. The method of claim 10, wherein the substrate is part of a finished product.

17. The method of claim 11, wherein the deposited layers of mixture are selectively melted to obtain a component having a predetermined porosity at predetermined locations.

18. The method of claim 10, wherein the selective melting step includes making multiple scans with the laser.

19. A method of building an orthopedic implant comprising the steps of:
    mixing a first powder having antimicrobial properties with a biocompatible second powder to form a mixture, at least the second powder being metallic;

depositing a layer of the mixture on top of a substrate; and selectively melting the mixture layer by making multiple scans with a laser.

20. The method claim 19, wherein the first powder is metallic.

21. The method of claim 19, further comprising depositing at least one additional layer of mixture and selectively melting the at least one additional layer.

22. The method of claim 19, wherein the first powder includes silver.

23. The method of claim 22, wherein the silver comprises approximately between 0.05% to 9.0% of the mixture.

24. The method of claim 21, wherein the steps of depositing at least one additional layer of the mixture and selectively melting the at least one additional layer of the mixture are repeated until an orthopedic implant is built.

25. The method of claim 21, further comprising depositing at least one layer of biocompatible powder onto either the substrate or a previous layer of the mixture and selectively melting the at least one layer of biocompatible powder.

26. The method of claim 19, wherein the substrate is part of a finished product.

27. The method of claim 21, wherein the deposited layers of mixture are selectively melted to obtain a component having a predetermined porosity at predetermined locations.

* * * * *